United States Patent
Pandolfino et al.

(10) Patent No.: US 12,390,152 B2
(45) Date of Patent: Aug. 19, 2025

(54) FOUR-DIMENSIONAL MANOMETRY

(71) Applicant: Northwestern University, Evanston, IL (US)

(72) Inventors: John E. Pandolfino, Wilmette, IL (US); Wenjun Kou, Rockford, IL (US); Neelesh A. Patankar, Buffalo Grove, IL (US); Dustin Carlson, Chicago, IL (US)

(73) Assignee: Northwestern University, Evanston, IL (US)

( * ) Notice: Subject to any disclaimer, the term of this patent is extended or adjusted under 35 U.S.C. 154(b) by 1056 days.

(21) Appl. No.: 17/309,262

(22) PCT Filed: Nov. 18, 2019

(86) PCT No.: PCT/US2019/061938
§ 371 (c)(1),
(2) Date: May 12, 2021

(87) PCT Pub. No.: WO2020/102793
PCT Pub. Date: May 22, 2020

(65) Prior Publication Data
US 2022/0117542 A1    Apr. 21, 2022

Related U.S. Application Data

(60) Provisional application No. 62/768,487, filed on Nov. 16, 2018.

(51) Int. Cl.
*A61B 5/00*     (2006.01)
*A61B 5/03*     (2006.01)
*A61B 5/0538*   (2021.01)

(52) U.S. Cl.
CPC ............ *A61B 5/4233* (2013.01); *A61B 5/037* (2013.01); *A61B 5/0538* (2013.01); *A61B 5/7425* (2013.01)

(58) Field of Classification Search
None
See application file for complete search history.

(56) References Cited

U.S. PATENT DOCUMENTS

| | | |
|---|---|---|
| 2004/0254495 A1 | 12/2004 | Mabary et al. |
| 2005/0065450 A1 | 3/2005 | Stuebe et al. |
| 2006/0095032 A1* | 5/2006 | Jackson .......... A61M 25/10184 606/41 |

(Continued)

OTHER PUBLICATIONS

Ghosh et al., Physiology of the Esophageal Pressure Transition Zone: Separate Contraction Waves Above and Below, Am J Physiol Gastrointest Liver Physiol, 2006, 290:G568-G576.

(Continued)

*Primary Examiner* — Aurelie H Tu
(74) *Attorney, Agent, or Firm* — Quarles & Brady LLP

(57) ABSTRACT

Described here are systems and methods for four-dimensional manometry, which can include generating and displaying rendering data that simultaneously depict spacetime variations in impedance, pressure, and esophageal luminal morphology. From these data, bolus tracking and esophageal opening and velocity data can be measured and visualized without the need for additional imaging, thereby reducing a subject's exposure to otherwise necessary ionizing radiation.

20 Claims, 11 Drawing Sheets

(56) References Cited

U.S. PATENT DOCUMENTS

| | | | |
|---|---|---|---|
| 2008/0154191 A1* | 6/2008 | Gobel | A61B 5/037 604/101.05 |
| 2008/0319350 A1* | 12/2008 | Wallace | A61B 5/0538 606/41 |
| 2010/0152607 A1 | 6/2010 | Kassab | |
| 2013/0035740 A1* | 2/2013 | Sharma | A61N 1/36178 607/40 |
| 2015/0073229 A1 | 3/2015 | Omari et al. | |
| 2015/0126837 A1 | 5/2015 | Kassab et al. | |
| 2017/0360369 A1* | 12/2017 | Geist | A61B 5/4233 |

OTHER PUBLICATIONS

Ghosh et al., Physiology of the Oesophageal Transition Zone in the Presence of Chronic Bolus Retention: Studies Using Concurrent High Resolution Manometry and Digital Fluoroscopy, Neurogastroenterology & Motility, 2008, 20(7):750-759.

International Searching Authority, International Search Report and Written Opinion, PCT/US2019/061938, Feb. 4, 2020, 15 pages.

Janssens et al., Peristalsis in Smooth Muscle Esophagus After Transection and Bolus Deviation, Gastroenterology, 1976, 71:1004-1009.

* cited by examiner

FOUR-DIMENSIONAL MANOMETRY

CROSS-REFERENCE TO RELATED APPLICATIONS

This application represents the U.S. national stage entry of International Patent Application Serial No. PCT/US2019/061938, filed on Nov. 18, 2019, and entitled "FOUR-DIMENSIONAL MANOMETRY," and claims the benefit of U.S. Provisional Patent Application Ser. No. 62/768,487, filed on Nov. 16, 2018, and entitled "FOUR-DIMENSIONAL ESOPHAGEAL IMPEDANCE MANOMETRY," the contents of each of which are herein incorporated by reference in their entirety for all purposes.

STATEMENT REGARDING FEDERALLY SPONSORED RESEARCH

This invention was made with government support under DK079902 awarded by the National Institutes of Health. The government has certain rights in the invention.

BACKGROUND

Esophageal impedance manometry measures impedance and pressure (e.g., esophageal luminal pressure). The data measured using esophageal impedance manometry can be used to evaluate the contraction function of the upper GI tract in many situations (e.g., breathing, swallowing food, swallowing liquid, drinking, coughing) and can be useful for diagnosing symptoms that originate in the esophagus.

Although esophageal impedance manometry provides information about motility through the esophagus, conventional techniques are unable to provide quantification of bolus emptying flux, emptying velocity, and wall stiffness. These data are important for evaluating esophagogastric junction ("EGJ") properties and function. A space-time concurrent esophageal morphology and pressure distribution is important for evaluating esophageal functions during swallowing tests, but these needs are unmet with current known technologies.

SUMMARY OF THE DISCLOSURE

The present disclosure addresses the aforementioned drawbacks by providing a method for generating a rendering simultaneously depicting space-time variations of impedance, pressure, an esophageal luminal morphology for an esophagus of a subject from which impedance data and pressure data have been measured. The method includes accessing with a computer system, impedance data and pressure data measured from a subject's esophagus; generating a superimposed impedance and pressure color map from the impedance and pressure data; processing the superimposed impedance and pressure color map to identify landmarks indicating at least one of an upper esophageal sphincter and a lower esophageal sphincter; generating spatial-temporal conductance data from the impedance data; computing spatial-temporal values of luminal liquid cross-sectional area based at least in part on the spatial-temporal conductance data; computing a luminal radius at each time point represented in the impedance data and the pressure data; generating from the impedance data, the pressure data, the spatial-temporal values of luminal liquid cross-sectional area, and the luminal radius at each time point, rendering data that simultaneously depicts space-time variations in impedance, pressure, and esophageal luminal morphology in the subject's esophagus; and displaying the rendering data to a user.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
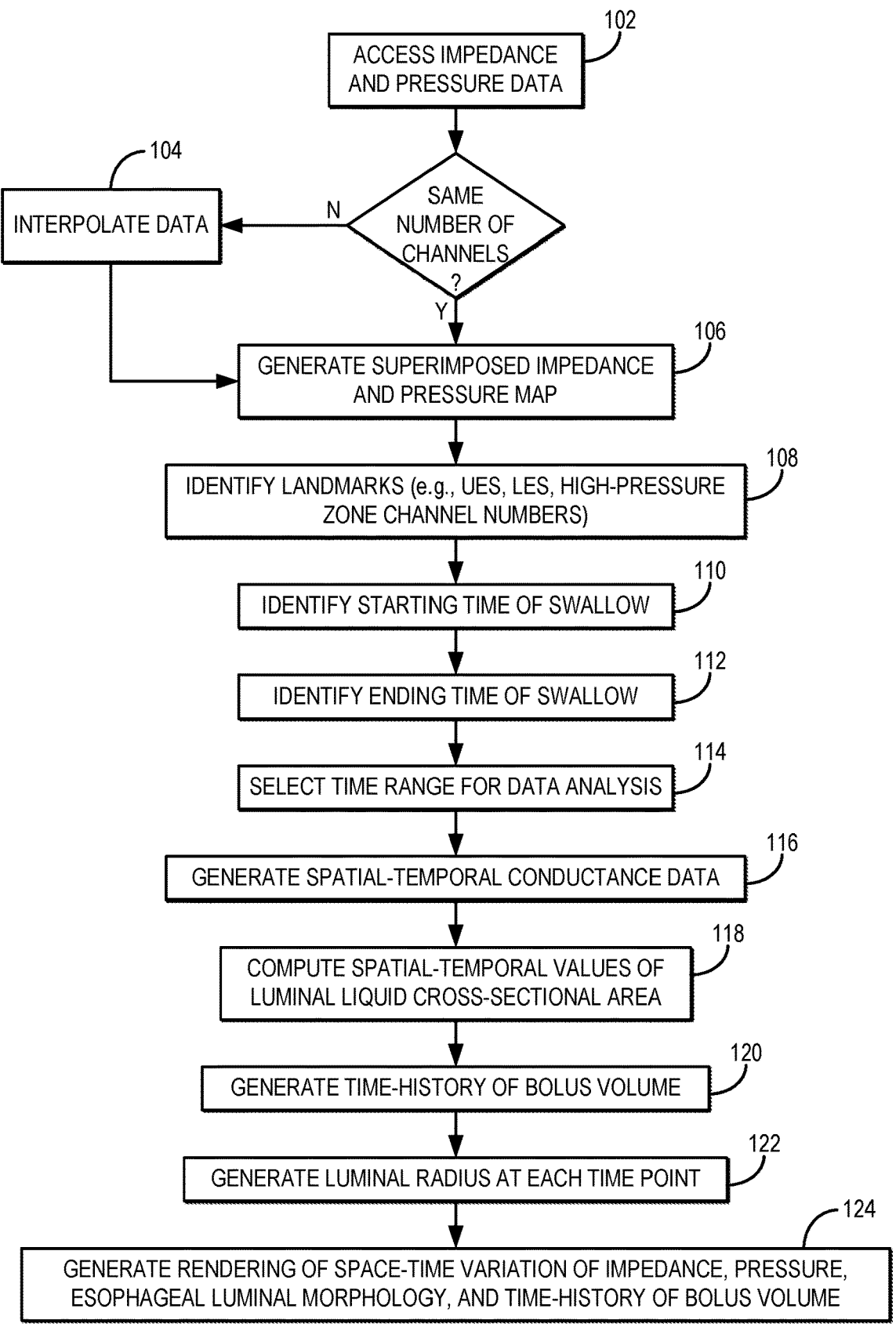
FIG. 1 is a flowchart setting forth the steps of an example method for generating a simultaneous rendering of space-time impedance, pressure, and esophageal luminal morphology from impedance pressure data recorded from a subject's esophagus.

Described here are systems and methods for four-dimensional ("4D") manometry (e.g., esophageal impedance manometry), which can include analyzing and displaying, visualizing, or otherwise presenting esophageal luminal diameter, impedance, and pressure data by combining a space-time domain with simultaneous impedance and pressure measures to derive volume descriptions and opening dimensions of the esophagus.

These impedance and pressure data can be measured or otherwise recorded using a suitable manometry system, which may include a probe or catheter that is inserted into the esophagus or upper gastrointestinal ("GI") tract. These systems measure impedance, pressure, or both, along different spatial positions in the esophagus or upper GI tract.

The systems and methods described in the present disclosure provide an improvement to measuring and visualizing data measured from the esophagus. Many of the variables recorded in conventional esophageal manometry studies are dichotomous and are not clinically useful because they do not describe the opening dimensions of the esophagogastric junction ("EGJ"). Having techniques for measuring the opening dimensions of the EGJ is important for evaluating patients with reflux and swallowing problems.

The systems and methods described in the present disclosure provide a technical improvement over existing techniques for esophageal impedance manometry by determining otherwise missing components of geometry and lumen opening. Lumen opening is an important feature that governs flow during swallowing and reflux. Another technical improvement is that current methods circumvent the need for in-vivo resistivity of bolus, which is challenging to obtain due to mixing between test fluid and esophageal luminal fluid. The method described in the present disclosure can deduce the effective in-vivo resistivity of liquid bolus, for instance, by matching predicted bolus volume and the known volume of the test liquid.

Moreover, the systems and methods described in the present disclosure provide a tool to construct space-time concurrent data on esophageal morphology, pressure, and impedance using high-resolution impedance-manometry measurements. The analysis further allows for calculation of time-history of bolus volume and retention volume, esophageal emptying flow and velocity, esophageal wall stiffness, and EGJ opening dimensions.

In general, the analysis includes mapping space-time impedance values of a concerned swallow to space-time luminal cross-sectional area ("CSA") data based on Ohm's law and biomechanical principles. Then, the analysis technique constructs a simultaneous rendering of space-time variation of pressure, impedance, and esophageal morphology, as well as the time-history of bolus volume (e.g., as one integrated movie or other visualizable data structure). The opening dynamics, bolus flow flux/velocity, distensibility within a chosen EGJ region, and other parameters can be calculated from this rendering to assess EGJ function and opening dynamics.

To this end, the systems and methods described in the present disclosure provide an innovative way to define the phases of bolus transit based on time-history of volume. They also provide a technique to calculate the time-history of bolus retention during the whole swallow that simulates fluoroscopy without the need for exposing a subject to ionizing radiation. Also provided is a technique to quantify esophageal emptying properties, such as duration of flow and flow gradients. The systems and methods described in the present disclosure also provide an integrated tool to analyze EGJ function and mechanical properties of opening during swallowing and reflux events.

Thus, the systems and methods described in the present disclosure improve upon current esophageal impedance manometry techniques by enabling the determination of a volume description and a geometry description that can be used to determine the lumen diameter through the EGJ. Another improvement includes the ability to track bolus flow dynamics without conducting additional imaging procedures that require ionizing radiation. The integrated four-dimensional rendering of esophageal luminal morphology, pressure, and impedance distribution generated by the systems and methods described in the present disclosure also advantageously describes the volume of retention and flow through the EGJ.

In some instances, the systems and methods described in the present disclosure provide four-dimensional manometry, in which a simultaneous rendering of space-time variations in impedance, pressure, and esophageal luminal morphology can be generated. The rendering data can be displayed to user or stored for further processing and analysis. For instance, the rendering data can be processed to analyze bolus transit to quantify the time-history of bolus retention volume and bolus transit characteristics. The rendering data can also be processed to analyze EGJ opening dynamics and bolus emptying velocity.

The analyses can be done on a per swallow basis. For each swallow, esophageal data (e.g., impedance data and pressure data) are accessed and processed by a computer system. The esophageal data may include high resolution impedance manometry ("HRIM") data. In one example study, such data were imported from ManoView (Given Imaging). The esophageal data may include pre-swallow recordings, such as around 3-8 seconds of pre-swallow recordings, in order to retain enough baseline data. Advantageously, the systems and methods described in the present disclosure can be implemented using any impedance manometry system that is capable of measuring measurements of impedance and pressure across the space-time domain. The imported data can be fed into the analysis along with several inputs, including the upper esophageal sphincter ("UES") channel number, the crural diaphragm ("CD") channel number, swallow starting time, and swallow ending time.

The impedance between the electrode pairs measures the opposition of electric current when it flows for a certain length. At low frequency, like the situation in HRIM measurements (100 Hz), the capacitive effects from surrounding tissue between the electrode pairs can be ignored, and the impedance can be equivalent to electric resistance. The electric resistance measured by electrode pairs includes three parts: esophageal gas resistance, conductance from surrounding materials including esophageal tissue and materials associated with the catheter, and esophageal liquids. Their collective effect can be described in terms of conductance (i.e., the inverse of the impedance):

$$\frac{1}{R} = G = G_g + G_t + G_l \cong G_t + G_l; \qquad (1)$$

where R is the resistance obtained from impedance readings; G is the total conductance; and $G_g$, $G_t$, and $G_l$ are the esophageal gas conductance (inverse of gas resistance), conductance from surrounding materials (e.g., esophageal tissue, catheter), and esophageal liquid conductance, respectively. The esophageal gas conductance, $G_g$, is typically minimal because of its high resistance compared with liquid and can therefore be ignored. The impedance of surrounding materials can include impedance of esophageal tissue and impedance associated with materials in the catheter. Esophageal tissue has a very high impedance for electrical insulation, whereas the impedance of materials used in the catheter are often lower and often referred to as "mucosal impedance" because the mucosal layer is the inner-most layer surrounding the catheter. Thus, the conductance of surrounding materials, $G_t$, is typically dominated by esophageal tissue conductance, and $G_t$ may also be referred to as mucosal conductance. For a "non-typical catheter," in which the catheter conductance cannot be ignored, the methods described in the present disclosure can be adapted such that $G_t$ becomes an "effective mucosal conductance" that incorporates the conductance from both esophageal tissue and the catheter. The esophageal liquid conductance, $G_l$, may also be referred to as bolus conductance. Based on Ohm's law, the conductance can be related to the cross-sectional area ("CSA") of bolus liquid within each electrode pair as, $$G_l(h, t) = \frac{CSA_l(h, t)}{r_l \times L}; \quad (2)$$

where $r_l$ is the resistivity of the liquid bolus; L is the distance between an electrode pair, which as one example may be 2 cm; and $CSA_l$ is the average CSA of bolus within the concerned electrode pair. Both $G_l$ and $CSA_l$ vary among different positions (e.g., channels), which can be labeled as h and time, which can be labeled as t. Similarly, the mucosal conductance, or effective mucosal conductance, can be expressed as, $$G_t(h, t) = \frac{CSA_t(h, t)}{r_t(h) \times L} \cong \frac{CSA_t(h)}{r_t(h) \times L} = G_t(h); \quad (3)$$

where $r_t(h)$ is the resistivity of the "effective: tissue conductance, which varies spatially (i.e., as a function of h) due to tissue inhomogeneity. As shown in Eqn. (3), the approximation of $CSA_t(h,t) \cong CSA_t(h)$ means that the CSA of the esophageal wall (or effective CSA that incorporates the influence from a non-typical catheter), though spatially inhomogeneous, does not vary temporally. This can be valid because the esophageal wall is a long tube and, thus, the large lateral dilation, lateral contraction, or both, causes minimal axial deformation. Consequently, the CSA can be approximately conserved based on the incompressibility of esophageal tissue, which means that if the average lumen diameter increases or decreases the esophageal wall thickness will accordingly decrease or increase, respectively.

Combining Eqns. (1)-(3) results in the following expression:

$$\frac{1}{R(h, t)} = G(h, t) \cong G_t(h) + G_l(h, t) = G_t(h) + \frac{CSA_l(h, t)}{r_l \times L}; \quad (4)$$

where R(h,t) can be taken as the measured impedance data, $r_l$ can be given based on test liquid properties (e.g., 0.812 ms/mm for 0.5 normal saline) or deduced based on the given volume of used liquids (e.g., using Eqn. (7) below), and L is the distance between electrode pairs, which in some non-limiting examples may be 2 cm. To compute $CSA_l(h,t)$, the mucosal conductance, $G_t(h)$, is first determined.

At each position, h, along the esophageal segment, the minimal impedance data measured over the time corresponds to the minimal luminal CSA. In many instances, the minimal luminal CSA may likely be zero; that is, $$\min_t CSA_l(h, t) \cong 0.$$

Thus, as one example mucosal conductance may be determined as, $$\begin{aligned} G_t(h) &= \left( G(h, t) - \frac{CSA_l(h, t)}{r_l \times L} \right) \\ &= \min_t \left( G(h, t) - \frac{CSA_l(h, t)}{r_l \times L} \right) \\ &\cong \min_t G(h, t) \\ &= \min_t \frac{1}{R(h, t)}. \end{aligned} \quad (5)$$

For abnormal cases, where minimal CSA is far from zero due to liquid residues (or even sensor malfunction), the mucosal conductance can be obtained by various different approaches. As some non-limiting examples, the mucosal conductance can be approximated by the mucosal conductance of neighboring channels, the median values of mucosal conductance of all channels, and the like. With $G_t(h)$ the luminal liquid CSA can be obtained based on Eqn. (4) as, $$CSA_l(h, t) = \left( \frac{1}{R(h, t)} - G_t(h) \right) \times r_l \times L. \quad (6)$$

With spatial-temporal values of luminal CSA, the bolus volume can be obtained by integrating the CSAs of all the channels along the esophageal body (e.g., from the upper esophageal sphincter ("UES") to the lower esophageal sphincter ("LES")). In particular, the volume of the swallowed bolus can be defined as the maximal bolus volume after swallow, but before emptying, as, $$Vol = \max_t V(t) = \\ \max_t \int_{LES}^{UES} CSA_l(h, t) dh = \left\{ \max_t \left( \frac{1}{R(h, t)} - G_t(h) \right) \times L \right\} \times \eta. \quad (7)$$

If the volume of the test liquid (i.e., the left-hand side of Eqn. (7)) is known, then the resistivity of liquid bolus in the actual in vivo condition, $r_l$, can be computed based on Eqn. (7).

Referring now to FIG. 1, a flowchart is illustrated as setting forth the steps of an example method for simultaneously rendering space-time variations of pressure, impedance, and esophageal luminal morphology. The method includes accessing, which a computer system, impedance data and pressure data that have been recorded or otherwise measured from a subject's esophagus, as indicated at step 102. Accessing the impedance data and pressure data with a computer system can include retrieving or otherwise accessing such data from a memory or other data storage device or medium. Accessing the impedance data and pressure data can include acquiring such data with a suitable measurement device, such as one or more esophageal or luminal catheters, and communicating that data to a computer system using a wired, wireless, or other type of connection. The impedance and pressure data can be such data that were recorded or otherwise measured over one or more swallows.

In some instances, the impedance data and the pressure data may have a different number of channels. In these instances, the lower channel data can be interpolated to match the number of channels in the higher channel data, as indicated at step 104. As one example, for each swallow, we 18-channel impedance data can be linearly interpolated to 36-channel data so that the interpolated impedance and pressure data are both temporally and spatially aligned.

A superimposed impedance and pressure map can be generated and displayed to a user, or otherwise stored for later use, as indicated at step 106. As one example, a plotted superimposed pressure and impedance color-map can be generated and displayed to a user, such as by displaying the color-map as part of a graphical user interface ("GUI").

Landmarks are then identified in the superimposed impedance and pressure map, as indicated at step 108. As one non-limiting example, three landmarks can be identified: an upper esophageal sphincter ("UES") channel number, a lower esophageal sphincter ("LES") channel number, and a high-pressure zone channel number.

The staring time of swallow is identified by processing the superimposed impedance and pressure map using the landmarks, as indicated at step 110. As an example the starting time of swallow can be identified based on impedance change, pressure change, or both, in the UES channel. The starting time of swallow is set as a reference time (i.e., time t=0).

Similarly, the ending time of swallow is identified by processing the superimposed impedance and pressure map using the landmarks, as indicated at step 112. For instance, the ending time of swallow can be identified based on LES restoration, or after a preselected duration of time, such as 12 seconds.

A time range for analyzing the impedance and pressure data is then selected using the starting and ending times of swallow, as indicated at step 114. For instance, the interested time range can be selected from three seconds before the swallowing starting time to the swallowing ending time.

Spatial-temporal conductance data are generated using the impedance data, as indicated at step 116. For channels above the LES channel, the mucosal conductance can be computed as the minimal value of total conductance along time using Eqn. (5). For channels below the LES channel (i.e., with potential residue liquid), the mucosal conductance can be approximated by the median value of mucosal conductance in the esophageal body.

The spatial-temporal values of luminal liquid CSA are then obtained, as indicated at step 118. These values can be computed using Eqn. (6) and the spatial-temporal conductance data. Based on the luminal liquid CSA, the time-history of bolus volume within the esophageal body can be computed, as indicated at step 120. Also, the luminal radius at each time and each channel, $R_{lumen}(h,t)$ can be obtained, as indicated at step 122. For example, the luminal radius can be computed based on known catheter radius, $R_{catheter}$, by assuming lumen of a circular shape, $$R_{lumen}(h, t) = \sqrt{\frac{CSA_l(h, t)}{\pi} + R_{catheter} \times R_{catheter}}. \quad (8)$$

With all of the above data, a simultaneous rendering of space-time variation of pressure, impedance, and esophageal luminal morphology, along with the time-history of bolus volume, can be generated, as indicated at step 124. This rendering can be displayed to a user or stored for later use.

As an example, the rendering can be displayed to a user as part of a GUI, which may be operable to enable a user to move through different time points to visualize and display different data contained within the rendering. The GUI may also be operable to display the rendering as a movie that plays through the relevant time points.

Using this generated rendering, other analyses can be carried out by the user. As one example, bolus transit analysis can be implemented to quantify the time-history of bolus retention volume and bolus transit characteristics. For instance, at each instant, the channel with the maximal pressure along the esophageal body can be identified as the contractile channel. The bolus retention volume can be defined as the volume of liquid above the contractile channel, and calculated by integrating bolus CSAs from the UES channel to the contractile channel at that instant. A time-history of bolus retention volume can then be obtained when the time is looped.

Similarly, the time-history of bolus volume within the esophageal body (i.e., above the crural diaphragm ("CD") channel) can be obtained and used to identify various phases of bolus transit, such as filling and accommodation, compartmentalization, esophageal emptying, and ampullary emptying. The emptying time can be defined as the duration of the phase of esophageal emptying. The emptying flux across the EGJ can be calculated as the change of bolus volume within the esophageal emptying phase divided by the emptying time.

Using the rendering generated as described above, EGJ analysis can also be implemented by the user to determine EGJ opening dynamics and bolus emptying velocity. For instance, an EGJ region-of-interest ("ROI") from 1 cm above the CD line to 1 cm below the CD line, and from three seconds prior to onset of the defined swallowing to 12 seconds later, can be defined. This ROI includes a channel below the CD, which is different from other bolus flow time ("BFT") protocols, which include the CD channel and two channels above the CD only. It is contemplated that including one channel below the CD to analyze EGJ opening will correlate better with bolus emptying from volume data. Then, the pressure data and bolus CSA data within the ROI (e.g., 3 channels, respectively), can be plotted in conjunction with the volume data for simultaneous analysis. An opening diameter can be introduced as the threshold, such that above this lumen diameter the lumen is considered to be open to allow bolus passage. The EGJ can be defined to be open when the diameter of all the three channels within the ROI are larger than the opening diameter. The criteria for defining EGJ opening can depend on the choice of the opening diameter, which could be optimized and validated based on diameter data in the esophageal emptying phase defined based on bolus volume data.

Figure 2A:
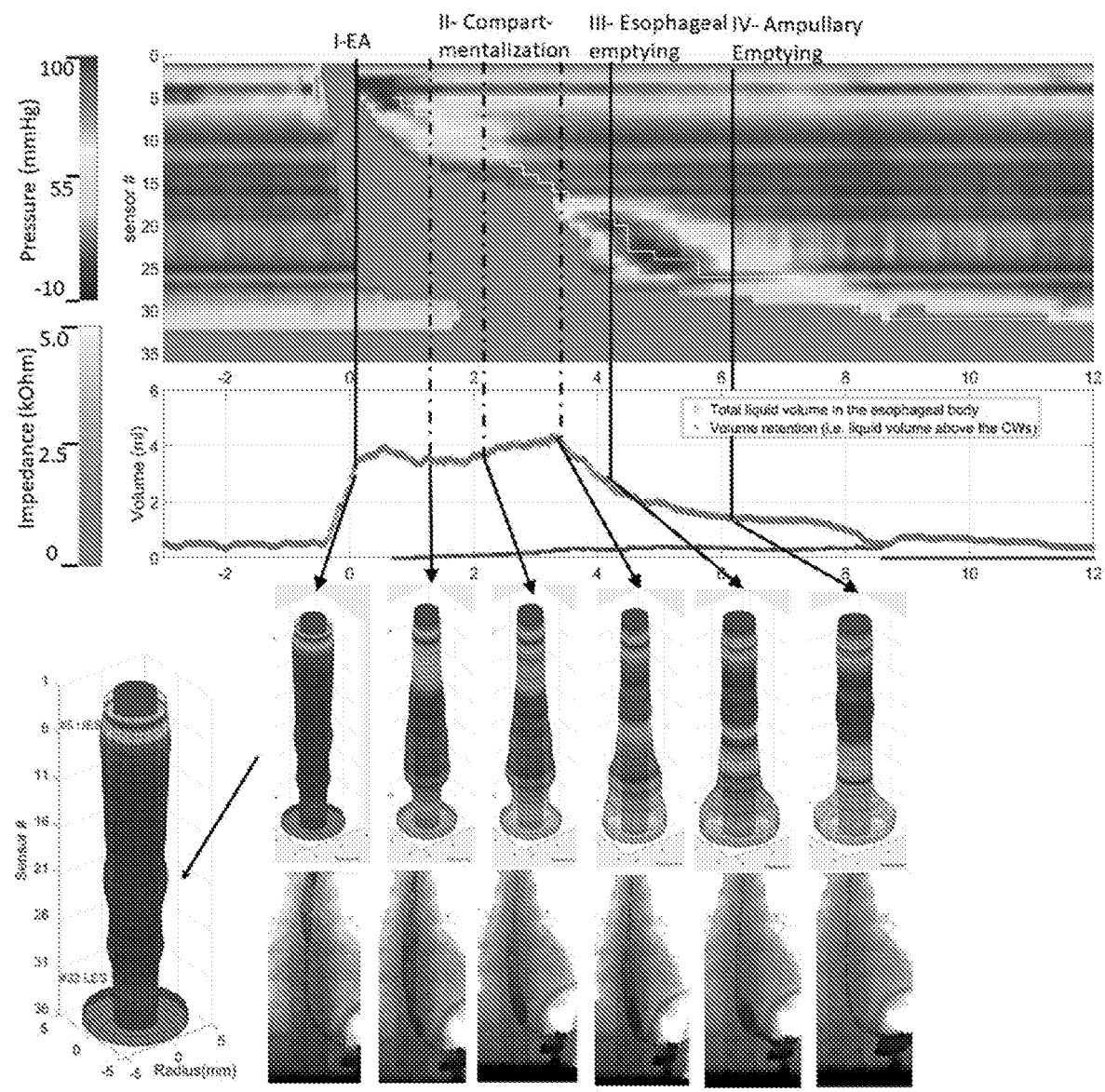
FIG. 2A illustrates an example graphical user interface displaying a superimposed impedance and pressure color map, a simultaneous rendering of space-time variations in impedance, pressure, and esophageal luminal morphology, and x-ray images of the subject from which the impedance and pressure data were obtained.
Figure 2B:
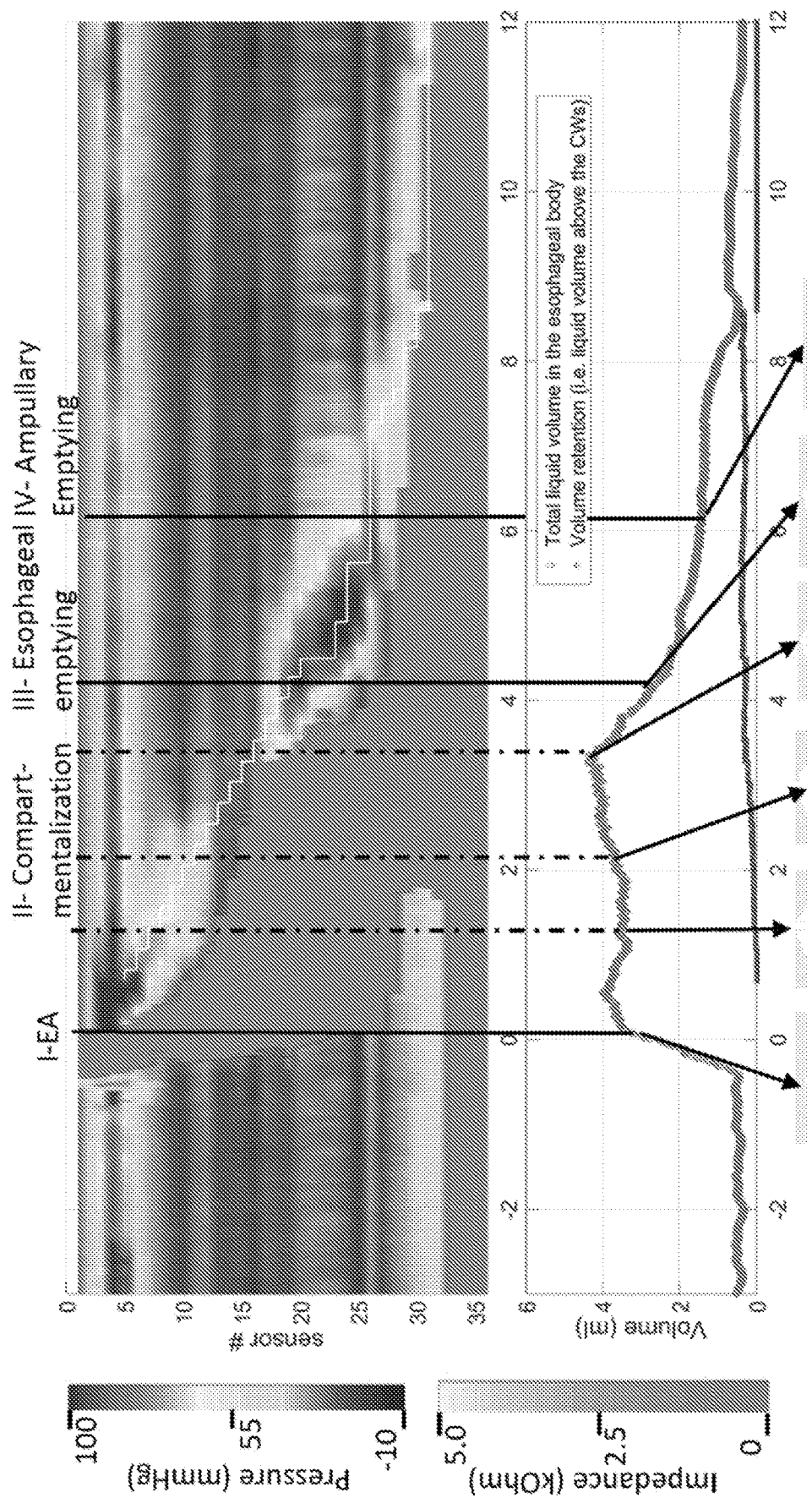
FIG. 2B illustrates the upper portion of FIG. 2A in more detail.
Figure 2C:
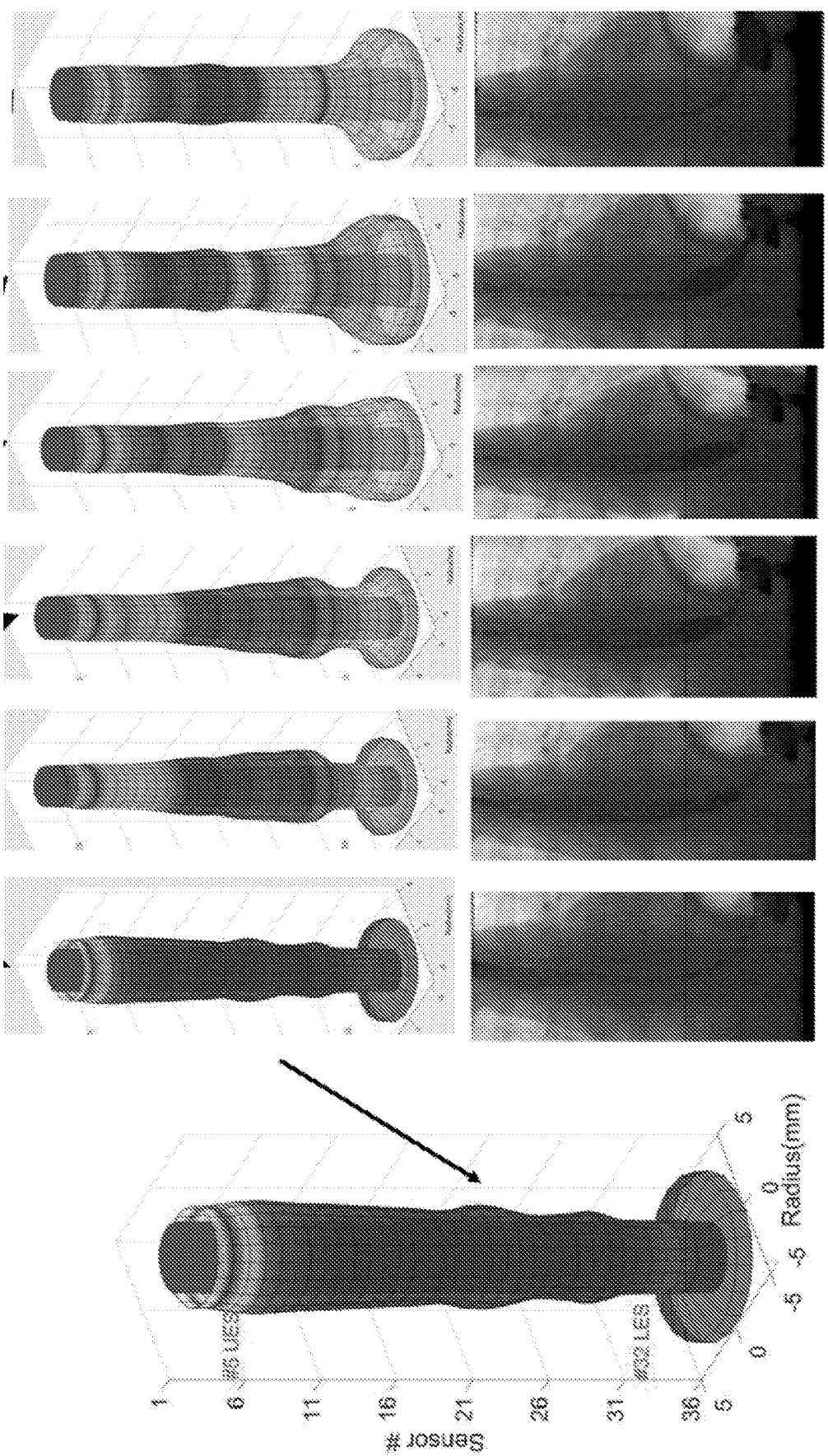
FIG. 2C illustrated the lower portion of FIG. 2B in more detail.

FIGS. 2A-2C illustrate an example graphical user interface displaying a superimposed impedance and pressure color map, a simultaneous rendering of space-time variations in impedance, pressure, and esophageal luminal morphology, and x-ray images of the subject from which the impedance and pressure data were obtained. FIGS. 2B and 2C show the upper and lower portions, respectively, of FIG. 2A in more detail. As shown in FIGS. 2A-2C, the systems and methods described in the present disclosure provide an improved visualization of impedance and pressure data in addition to volume and geometry changes in esophageal luminal morphology. As described above, these data can also be combined in a data structure to enable computation and monitoring of bolus tracking dynamics and esophageal dynamics (e.g., EGJ dynamics) and flow velocity, all without the need for imaging the subject with ionizing radiation.

Figure 3A:
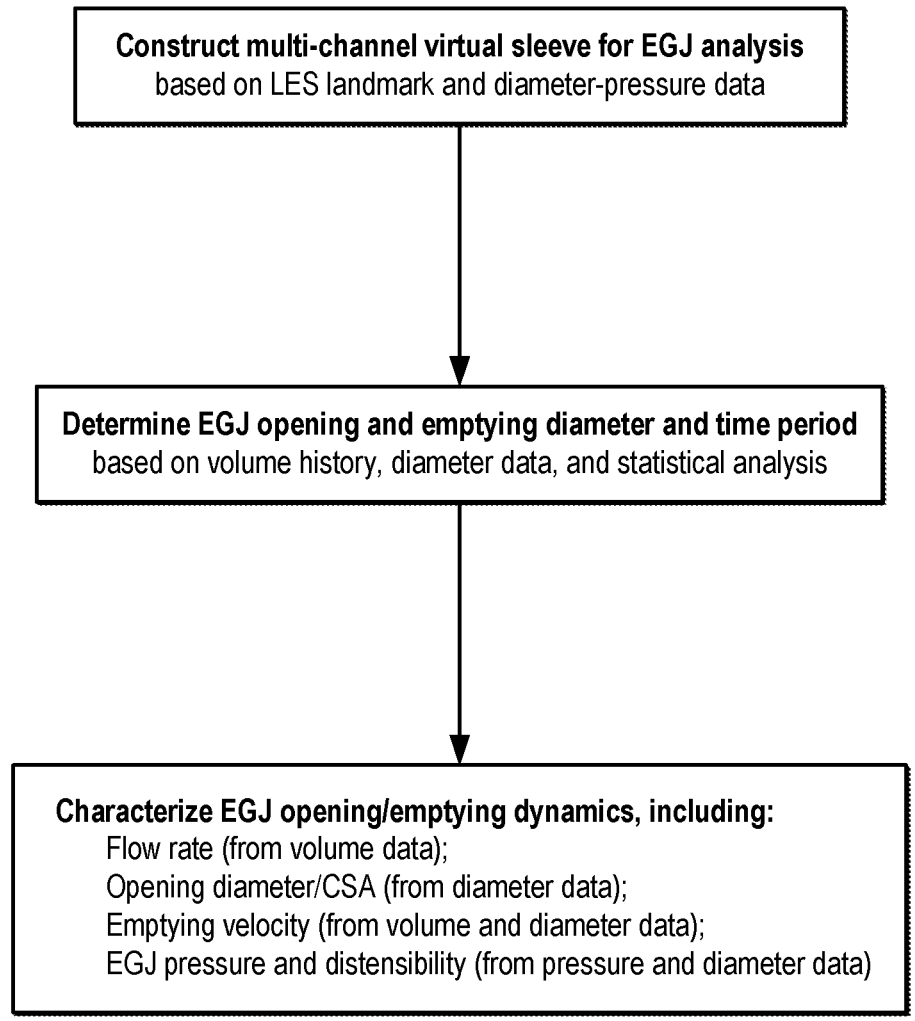
FIGS. 3A and 3B show an example analysis of esophagogastric junction ("EGJ") constructing a multiple-channel sleeve, or volume, for EGJ analysis with volume, diameter, and pressure data. EGJ opening/emptying diameter and time period are determined. Esophageal emptying flow rate, emptying velocity, EGJ opening period, and EGJ distensibility during emptying are also computed.
Figure 3B:
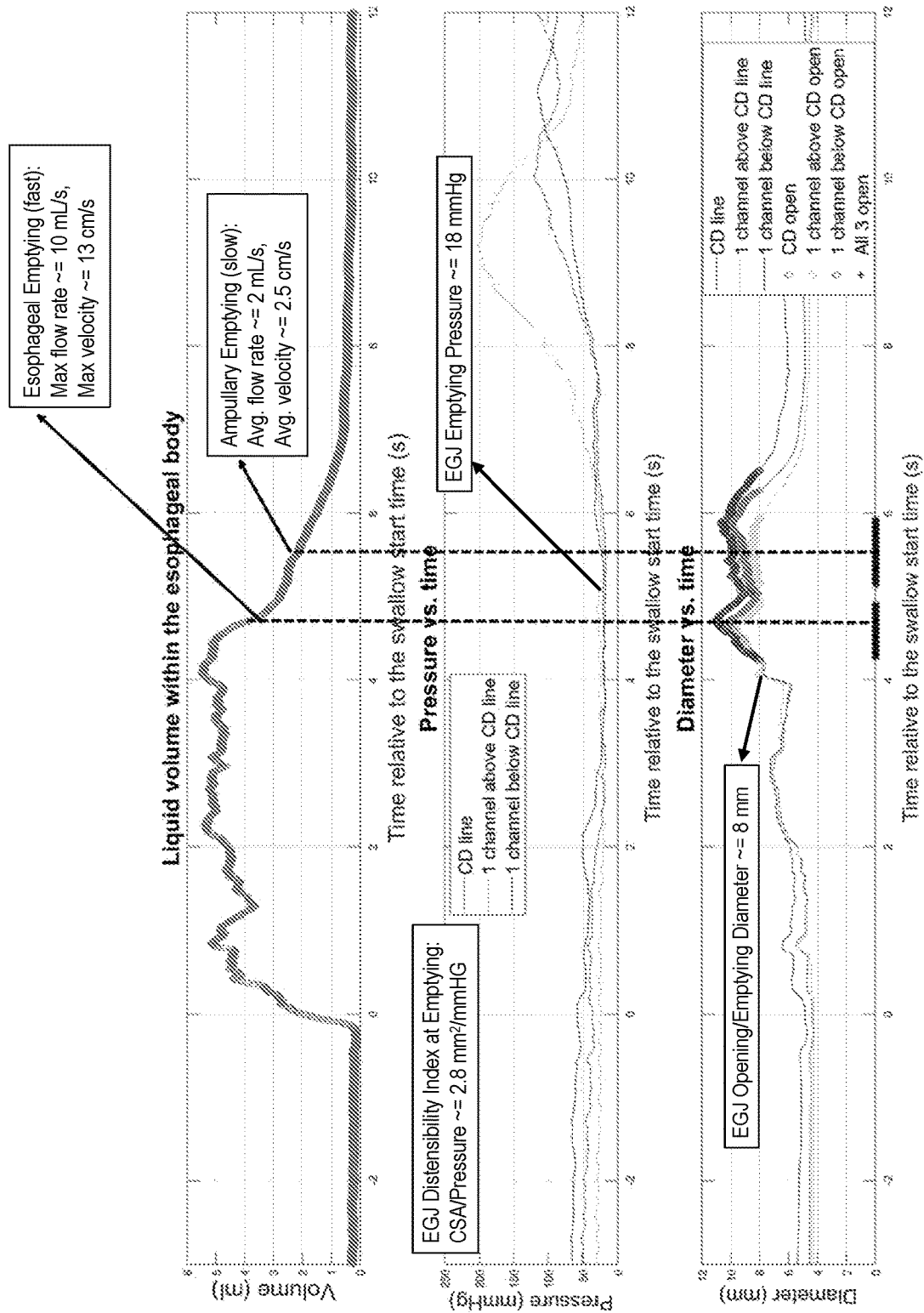

FIGS. 3A and 3B illustrate an example analysis of EGJ about a normal swallow. Based on an identified LES landmark and derived volume, diameter, and pressure data, a multi-channel virtual sleeve for EGJ is first constructed. EGJ opening/emptying diameter and period can then be determined based on volume, diameter data, and statistical analysis. Then the flow rate and emptying velocity can be calculated. EGJ opening/emptying period and pressure can also be obtained and used to evaluate EGJ distensibility during emptying.

Thus, systems and methods for 4D manometry have been described. Compared with conventional manometry or impedance analysis, the 4D manometry described in the present disclosure enables a quantitative approach on information extraction from impedance data and further provides comprehensive characterization of temporal-spatial dynamics of bolus transit as well as esophageal wall behavior, in conjunction with simultaneous pressure data. Moreover, methods for 4D manometry circumvent the challenge of measuring bolus' resistivity in-vivo, which is complicated by the mixing between test liquid and liquid constituents within the esophageal lumen.

As described, analysis of 4D manometry also provides several additional insights. As one example, visualizing luminal geometry concurrent with pressure illustrates how the bolus transit pattern is modulated by muscular contractions. For instance, in healthy subjects, LES relaxation can initiate the EGJ outflow, whereas in achalasia, the non-relaxing LES can be a significant determinant of EGJ outflow obstruction. As another example, 4D manometry can extend previous qualitative impedance analyses of incomplete bolus transit to quantitative measures of retained bolus volume, from which one can visualize retention volume and location. As still another example, 4D manometry can enable direct illustration of EGJ diameter dynamics and prediction on flow rate, which provides a quantitative evaluation of esophageal emptying and reflux.

Mucosal impedance is another characterization of a tissue property that can complement tissue stiffness like distensibility. As described above, such as with respect to Eqn. (5), the mucosal impedance at each esophageal position can be predicted as the maximal impedance during per-swallow period. It is contemplated that this condition will be valid when the pre-swallow bolus residual is minimal (i.e., near zero). In cases like Type-II Achlasia, however, it is contemplated that the pre-swallow residual will be significant within the lower esophageal region. This region is referred to as the residual region, whereas the remaining region of esophagus (i.e., the upper region or EGJ region) as the non-residual region. In cases with a residual region, the mucosal impedance of the whole region can be obtained as follow.

First, the residual and the non-residual regions are determined based on minimal impedance during pre-swallow period. As an example, a cut-off value of 1 kOhm can be used. The mucosal impedance in the non-residual region can then be computed using Eqn. (5). The mucosal impedance in the residual region can then be extrapolated based on values in the neighboring non-residual region.

The methods described in the present disclosure work even for cases where a non-typical catheter, whose conductance cannot be ignored, is used. This is because the impact on the conductance from both esophageal tissue and catheter are time-independent and thus can be compensated by comparing values at two or more time points, illustrated in Eqns. (5) and (6). In such instances, the mucosal conductance can be treated as an effective conductance that also includes the contributions from the catheter.

Figure 4A:
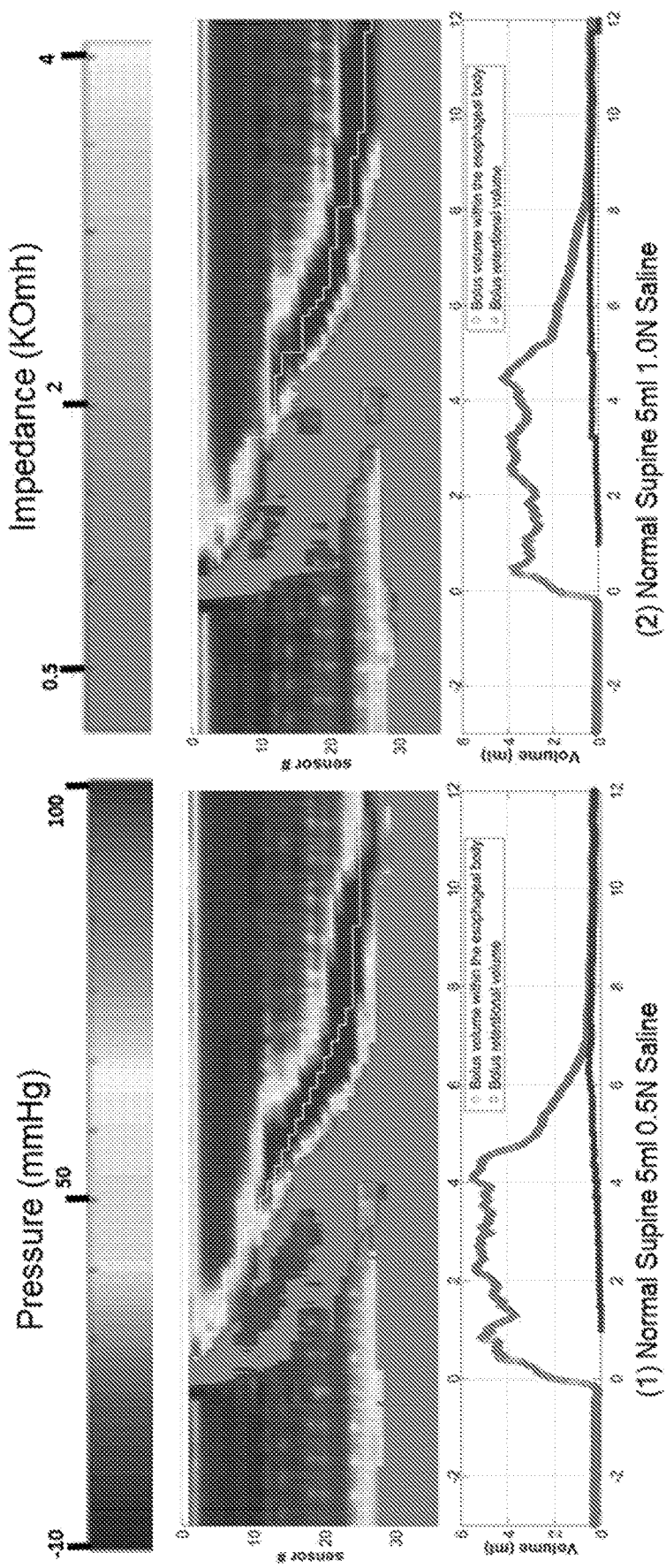
FIGS. 4A-4C show examples of pressure-impedance topography concurrent with bolus transit history of various cases, including (1) a normal supine subject with 5 ml 0.5 N saline bolus and (2) a normal supine subject with 5 ml 1.0 N saline bolus (FIG. 4A); (3) a normal upright subject with 5 ml 0.5 N saline bolus and (4) a normal upright subject with 5 ml 1.0 N saline bolus (FIG. 4B); and (5) a normal supine subject with 30 ml 0.5 N saline bolus and (6) a Type II Achlasia upright subject with 5 ml 0.5 N saline bolus.
Figure 4B:
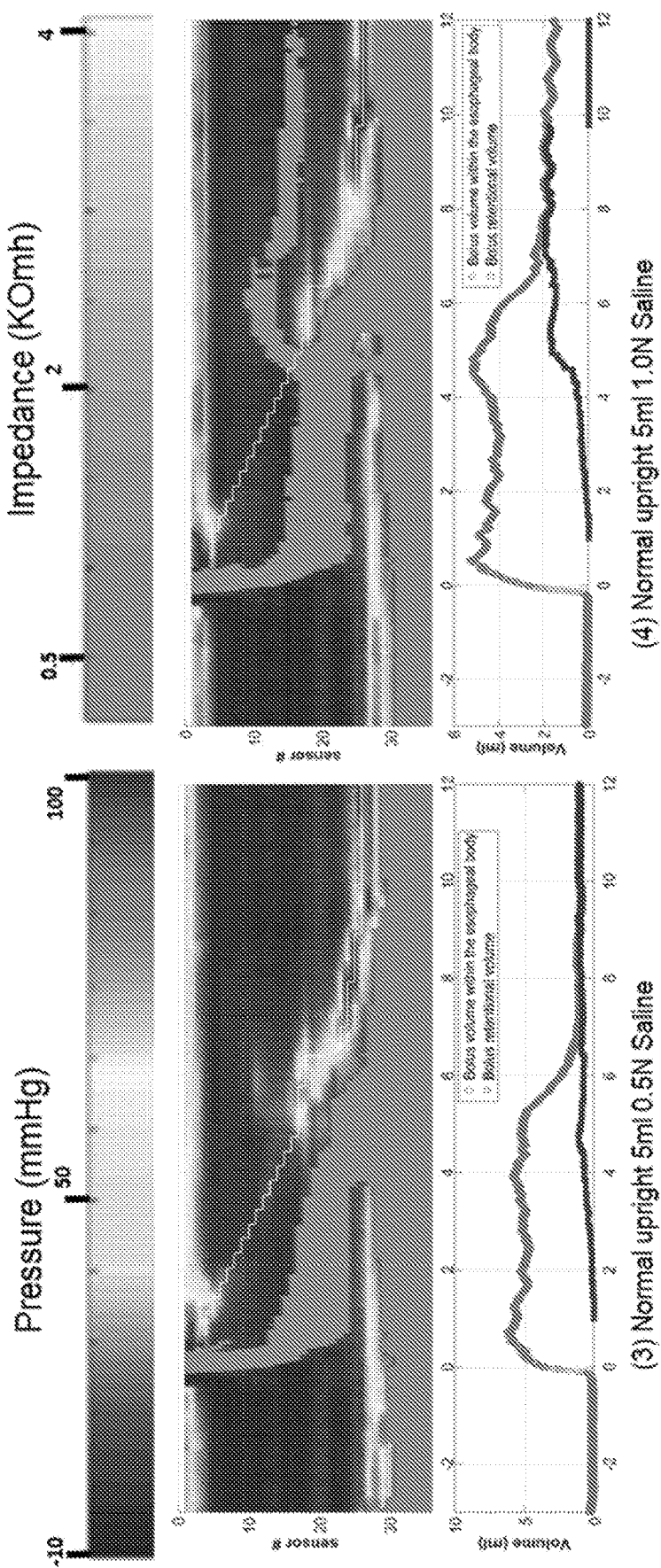
Figure 4C:
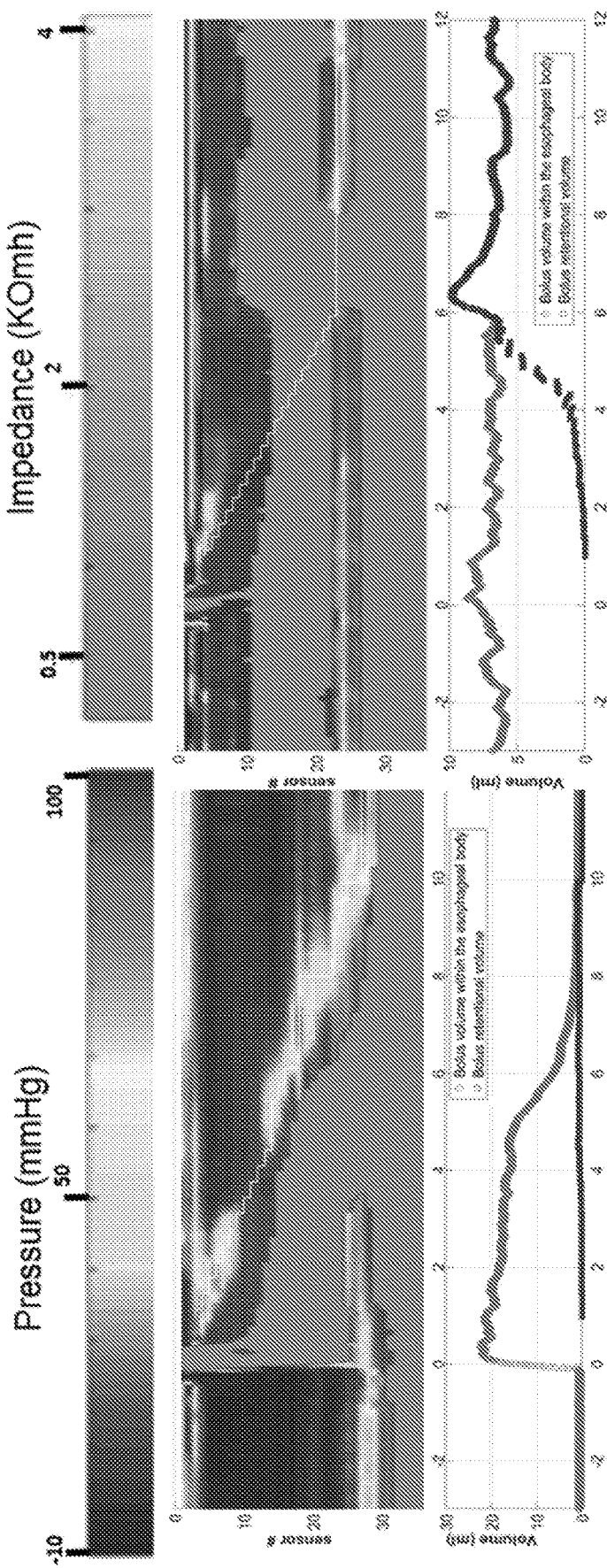

FIGS. 4A-4C show examples of pressure-impedance topography concurrent with bolus transit history of various cases. The bolus volume within the body can be defined as the total volume of predicted liquid bolus between UES and LES channels at each time stamp. The retentional, or residual, volume can be defined as described above.

Figure 5:
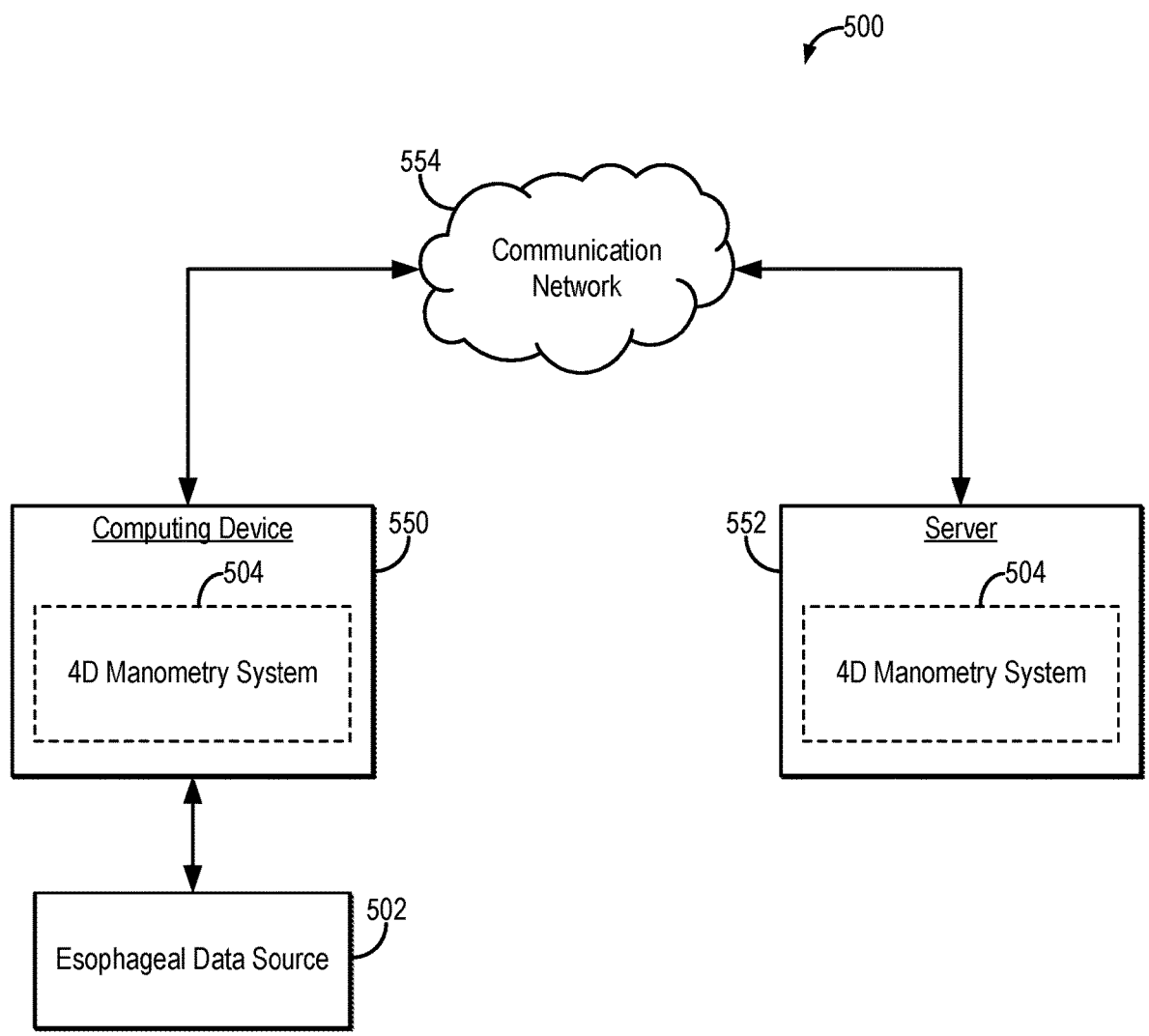
FIG. 5 is a block diagram of an example system that can implement a four-dimensional manometry system to generate a simultaneous rendering of space-time impedance, pressure, and esophageal luminal morphology.

Referring now to FIG. 5, an example of a system 500 for generating simultaneous rendering of space-time variation of pressure, impedance, and esophageal luminal morphology in accordance with some embodiments of the systems and methods described in the present disclosure is shown. As shown in FIG. 5, a computing device 550 can receive one or more types of data (e.g., impedance data, pressure data) from esophageal data source 502, which may be an esophageal catheter or a memory or other data storage device or medium on which esophageal data are stored. In some embodiments, computing device 550 can execute at least a portion of a four-dimensional manometry system 504 to generate a simultaneous rendering of space-time variation of pressure, impedance, and esophageal luminal morphology from data received from the esophageal data source 502.

Additionally or alternatively, in some embodiments, the computing device 550 can communicate information about data received from the esophageal data source 502 to a server 552 over a communication network 554, which can execute at least a portion of the four-dimensional manometry system 504 to generate a simultaneous rendering of space-time variation of pressure, impedance, and esophageal luminal morphology from data received from the esophageal data source 502. In such embodiments, the server 552 can return information to the computing device 550 (and/or any other suitable computing device) indicative of an output of the four-dimensional manometry system 504 to generate a simultaneous rendering of space-time variation of pressure, impedance, and esophageal luminal morphology from data received from the esophageal data source 502.

In some embodiments, computing device 550 and/or server 552 can be any suitable computing device or combination of devices, such as a desktop computer, a laptop computer, a smartphone, a tablet computer, a wearable computer, a server computer, a virtual machine being executed by a physical computing device, and so on. The computing device 550 and/or server 552 can also generate images, color maps, renderings, and other display elements or visualizable data structures from the data.

In some embodiments, esophageal data source 502 can be any suitable source of esophageal data (e.g., impedance measurement data, pressure measurement data), such as an esophageal catheter, another computing device (e.g., a server storing esophageal data), and so on. In some embodiments, esophageal data source 502 can be local to computing device 550. For example, esophageal data source 502 can be incorporated with computing device 550 (e.g., computing device 550 can be configured as part of a device for capturing, scanning, and/or storing esophageal data). As another example, esophageal data source 502 can be connected to computing device 550 by a cable, a direct wireless link, and so on. Additionally or alternatively, in some embodiments, esophageal data source 502 can be located locally and/or remotely from computing device 550, and can communicate data to computing device 550 (and/or server 552) via a communication network (e.g., communication network 554).

In some embodiments, communication network 554 can be any suitable communication network or combination of communication networks. For example, communication network 554 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 554 can be a local area network, a wide area network, a public network (e.g., the Internet), a private or semi-private network (e.g., a corporate or university intranet), any other suitable type of network, or any suitable combination of networks. Communications links shown in FIG. 5 can each be any suitable communications link or combination of communications links, such as wired links, fiber optic links, Wi-Fi links, Bluetooth links, cellular links, and so on.

Figure 6:
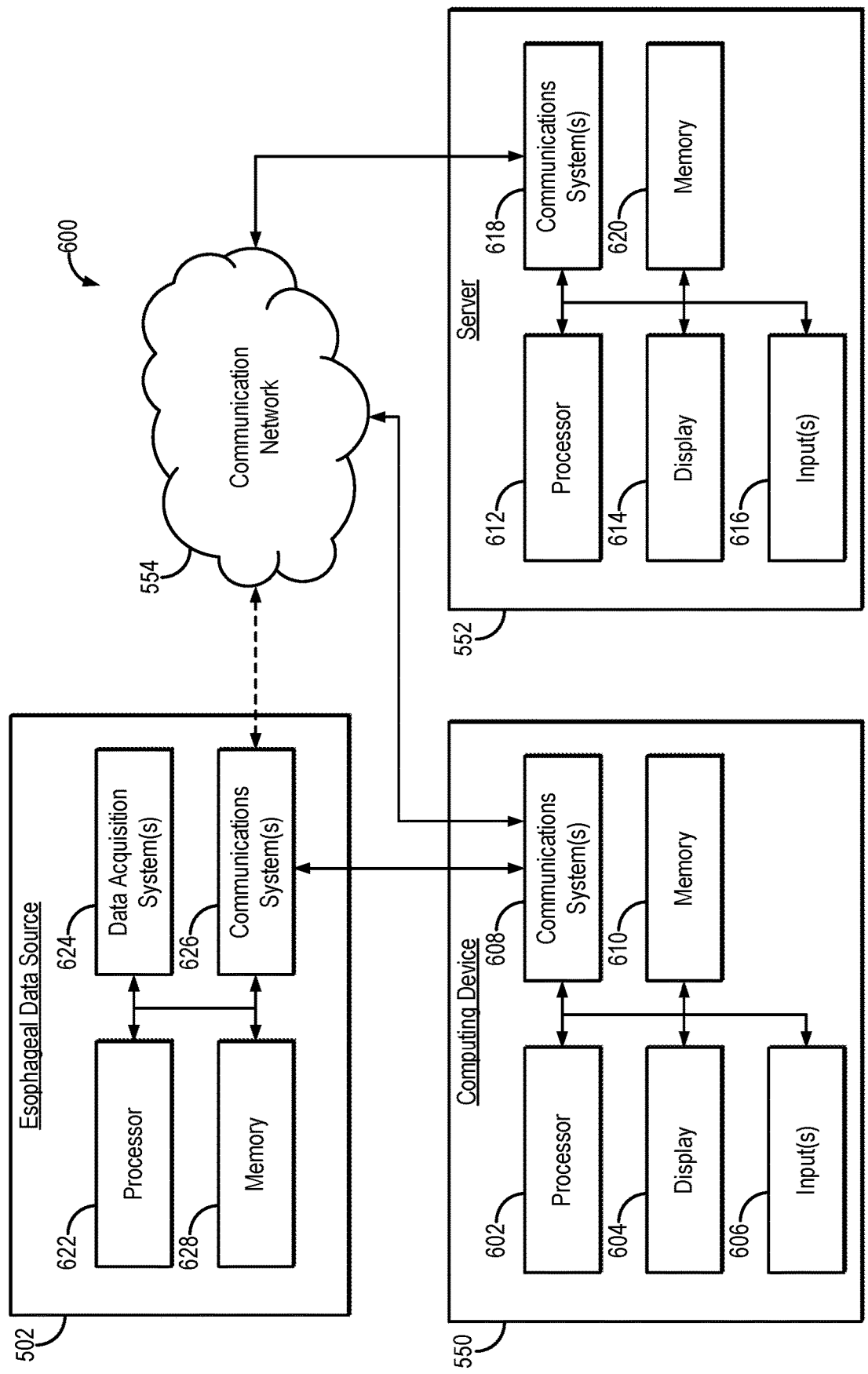
FIG. 6 is a block diagram of example hardware that can implement the system of FIG. 5.

Referring now to FIG. 6, an example of hardware 600 that can be used to implement esophageal data source 502, computing device 550, and server 552 in accordance with some embodiments of the systems and methods described in the present disclosure is shown. As shown in FIG. 6, in some embodiments, computing device 550 can include a processor 602, a display 604, one or more inputs 606, one or more communication systems 608, and/or memory 610. In some embodiments, processor 602 can be any suitable hardware processor or combination of processors, such as a central processing unit ("CPU"), a graphics processing unit ("GPU"), and so on. In some embodiments, display 604 can include any suitable display devices, such as a computer monitor, a touchscreen, a television, and so on. In some embodiments, inputs 606 can include any suitable input devices and/or sensors that can be used to receive user input, such as a keyboard, a mouse, a touchscreen, a microphone, and so on.

In some embodiments, communications systems 608 can include any suitable hardware, firmware, and/or software for communicating information over communication network 554 and/or any other suitable communication networks. For example, communications systems 608 can include one or more transceivers, one or more communication chips and/or chip sets, and so on. In a more particular example, communications systems 608 can include hardware, firmware and/or software that can be used to establish a Wi-Fi connection, a Bluetooth connection, a cellular connection, an Ethernet connection, and so on.

In some embodiments, memory 610 can include any suitable storage device or devices that can be used to store instructions, values, data, or the like, that can be used, for example, by processor 602 to present content using display 604, to communicate with server 552 via communications system(s) 608, and so on. Memory 610 can include any suitable volatile memory, non-volatile memory, storage, or any suitable combination thereof. For example, memory 610 can include RAM, ROM, EEPROM, one or more flash drives, one or more hard disks, one or more solid state drives, one or more optical drives, and so on. In some embodiments, memory 610 can have encoded thereon, or otherwise stored therein, a computer program for controlling operation of computing device 550. In such embodiments, processor 602 can execute at least a portion of the computer program to present content (e.g., images, user interfaces, graphics, tables), receive content from server 552, transmit information to server 552, and so on.

In some embodiments, server 552 can include a processor 612, a display 614, one or more inputs 616, one or more communications systems 618, and/or memory 620. In some embodiments, processor 612 can be any suitable hardware processor or combination of processors, such as a CPU, a GPU, and so on. In some embodiments, display 614 can include any suitable display devices, such as a computer monitor, a touchscreen, a television, and so on. In some embodiments, inputs 616 can include any suitable input devices and/or sensors that can be used to receive user input, such as a keyboard, a mouse, a touchscreen, a microphone, and so on.

In some embodiments, communications systems 618 can include any suitable hardware, firmware, and/or software for communicating information over communication network 554 and/or any other suitable communication networks. For example, communications systems 618 can include one or more transceivers, one or more communication chips and/or chip sets, and so on. In a more particular example, communications systems 618 can include hardware, firmware and/or software that can be used to establish a Wi-Fi connection, a Bluetooth connection, a cellular connection, an Ethernet connection, and so on.

In some embodiments, memory 620 can include any suitable storage device or devices that can be used to store instructions, values, data, or the like, that can be used, for example, by processor 612 to present content using display 614, to communicate with one or more computing devices 550, and so on. Memory 620 can include any suitable volatile memory, non-volatile memory, storage, or any suitable combination thereof. For example, memory 620 can include RAM, ROM, EEPROM, one or more flash drives, one or more hard disks, one or more solid state drives, one or more optical drives, and so on. In some embodiments, memory 620 can have encoded thereon a server program for controlling operation of server 552. In such embodiments, processor 612 can execute at least a portion of the server program to transmit information and/or content (e.g., data, images, a user interface) to one or more computing devices 550, receive information and/or content from one or more computing devices 550, receive instructions from one or more devices (e.g., a personal computer, a laptop computer, a tablet computer, a smartphone), and so on.

In some embodiments, esophageal data source 502 can include a processor 622, one or more data acquisition systems 624, one or more communications systems 626, and/or memory 628. In some embodiments, processor 622 can be any suitable hardware processor or combination of processors, such as a CPU, a GPU, and so on. In some embodiments, the one or more data acquisition systems 624 are generally configured to acquire data, images, or both, and can include impedance sensors, pressure sensors, pH sensors, ultrasound transducers, or combinations thereof. Additionally or alternatively, in some embodiments, one or more data acquisition systems 624 can include any suitable hardware, firmware, and/or software for coupling to and/or controlling operations of an esophageal catheter. In some embodiments, one or more portions of the data acquisition systems 624 can be removable and/or replaceable.

Note that, although not shown, esophageal data source 502 can include any suitable inputs and/or outputs. For example, esophageal data source 502 can include input devices and/or sensors that can be used to receive user input, such as a keyboard, a mouse, a touchscreen, a microphone, a trackpad, a trackball, and so on. As another example, esophageal data source 502 can include any suitable display devices, such as a computer monitor, a touchscreen, a television, etc., one or more speakers, and so on.

In some embodiments, communications systems 626 can include any suitable hardware, firmware, and/or software for communicating information to computing device 550 (and, in some embodiments, over communication network 554 and/or any other suitable communication networks). For example, communications systems 626 can include one or more transceivers, one or more communication chips and/or chip sets, and so on. In a more particular example, communications systems 626 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 628 can include any suitable storage device or devices that can be used to store instructions, values, data, or the like, that can be used, for example, by processor 622 to control the one or more data acquisition systems 624, and/or receive data from the one or more data acquisition systems 624; to generate images from esophageal data; present content (e.g., images, a user interface) using a display; communicate with one or more computing devices 550; and so on. Memory 628 can include any suitable volatile memory, non-volatile memory, storage, or any suitable combination thereof. For example, memory 628 can include RAM, ROM, EEPROM, one or more flash drives, one or more hard disks, one or more solid state drives, one or more optical drives, and so on. In some embodiments, memory 628 can have encoded thereon, or otherwise stored therein, a program for controlling operation of esophageal data source 502. In such embodiments, processor 622 can execute at least a portion of the program to generate images, transmit information and/or content (e.g., data, images, renderings) to one or more computing devices 550, receive information and/or content from one or more computing devices 550, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for generating a rendering simultaneously depicting space-time variations of impedance, pressure, an esophageal luminal morphology for an esophagus of a subject from which impedance data and pressure data have been measured, the method comprising:
   (a) acquiring impedance data and pressure data using an esophageal catheter having multiple channels that measure the impedance data and the pressure data along different spatial positions from a subject's esophagus, and communicating the impedance data and the pressure data to a computer system;
   (b) generating spatial-temporal conductance data from the impedance data using the computer system;
   (c) computing, with the computer system, spatial-temporal values of luminal liquid cross-sectional area based at least in part on the spatial-temporal conductance data;
   (d) computing, with the computer system, a luminal radius at each time point represented in the impedance data and the pressure data, wherein the luminal radius is computed in part using a known radius of the esophageal catheter used to acquire the impedance data and the pressure data;
   (e) generating, from the impedance data, the pressure data, the spatial-temporal values of luminal liquid cross-sectional area, and the luminal radius at each time point, rendering data that simultaneously depict space-time variations in impedance, pressure, and esophageal luminal morphology in the subject's esophagus; and
   (f) displaying the rendering data to a user using the computer system.

2. The method of claim 1, further comprising: generating from the rendering data, bolus retention volume data that quantify a time-history of bolus retention volume.

3. The method of claim 2, wherein the time-history of bolus retention volume is computed based on the spatial-temporal values of luminal liquid cross-sectional area.

4. The method of claim 3, wherein computing the time-history of bolus retention volume includes computing a bolus retention volume value for each time point by:
   generating a superimposed impedance and pressure color map from the impedance and pressure data;
   processing the superimposed impedance and pressure color map to identify an upper esophageal sphincter (UES) channel;
   processing the pressure data to identify a contractile channel as a channel with maximal pressure along the subject's esophagus; and
   computing the bolus retention volume value for a given time point by integrating the spatial-temporal values of luminal liquid cross-sectional area from the UES channel to the contractile channel for that given time point.

5. The method of claim 4, further comprising: interpolating at least one of the impedance data or the pressure data to a selected number of channels before generating the superimposed impedance and the pressure color map.

6. The method of claim 1, further comprising: generating from the rendering data, bolus transit data that quantify bolus transit characteristics.

7. The method of claim 1, further comprising: generating from the rendering data, time-history of bolus volume data that quantify time-history of bolus volume.

8. The method of claim 1, further comprising: generating from the rendering data, esophagogastric junction (EGJ) opening data that quantify EGJ opening dynamics.

9. The method of claim 8, wherein generating the EGJ opening data includes:
   generating a superimposed impedance and pressure color map from the impedance and pressure data;

processing the superimposed impedance and pressure color map to identify a crural diaphragm (CD) channel;

defining a region-of-interest (ROI) based on the CD channel; and computing the EGJ opening data based on pressure data and luminal liquid cross-sectional area within the ROI.

10. The method of claim 9, wherein the ROI includes the CD channel and at least one channel above the CD channel and at least one channel below the CD channel.

11. The method of claim 10, wherein the ROI is a spatial-temporal ROI defined from 3 seconds prior to onset of a swallow to 12 seconds after the onset of the swallow.

12. The method of claim 9, wherein the EGJ opening data are computed from the pressure data and luminal liquid cross-sectional area within the ROI based on a threshold opening diameter.

13. The method of claim 9, further comprising: interpolating at least one of the impedance data or the pressure data to a selected number of channels before generating the superimposed impedance and pressure color map.

14. The method of claim 1, further comprising: generating from the rendering data, bolus emptying velocity data that quantify bolus emptying velocity.

15. The method of claim 1, further comprising:

generating a superimposed impedance and pressure color map from the impedance and pressure data; and processing the superimposed impedance and pressure color map to identify a lower esophageal sphincter (LES) channel.

16. The method of claim 15, wherein generating spatial-temporal conductance data from the impedance data includes:

for channels above the LES channel, computing conductance values as a minimal value of total conductance along time; and for channels below the LES channel, computing conductance values as a median value of conductance in the subject's esophagus.

17. The method of claim 15, further comprising: interpolating at least one of the impedance data or the pressure data to a selected number of channels before generating the superimposed impedance and pressure color map.

18. The method of claim 1, wherein the luminal radius at each time point is computed using the spatial-temporal values of luminal liquid cross-sectional area and the known radius of the esophageal catheter used to acquire the pressure data and the impedance data.

19. The method of claim 1, wherein displaying the rendering data to the user comprises generating a graphical user interface (GUI) with the computer system and displaying the rendering data in conjunction with the GUI.

20. The method of claim 1, further comprising: generating from the rendering data, at least one of bolus conductivity or bolus resistivity based on a predicted bolus volume and a liquid bolus test volume.

* * * * *